United States Patent
Levine

(10) Patent No.: US 9,408,957 B1
(45) Date of Patent: Aug. 9, 2016

(54) BREAST PUMP SHIELD

(71) Applicant: Sherri Levine, Bradenton, FL (US)

(72) Inventor: Sherri Levine, Bradenton, FL (US)

(*) Notice: Subject to any disclaimer, the term of this patent is extended or adjusted under 35 U.S.C. 154(b) by 0 days.

(21) Appl. No.: 14/311,848

(22) Filed: Jun. 23, 2014

(51) Int. Cl.
*A61M 1/06* (2006.01)
*A61J 13/00* (2006.01)

(52) U.S. Cl.
CPC .............. *A61M 1/064* (2014.02); *A61M 1/062* (2014.02); *A61J 13/00* (2013.01)

(58) Field of Classification Search
CPC ....... A61M 1/06; A61M 1/064; A61M 1/066; A61M 1/068; A61J 9/08; A61J 9/085; A61J 13/00
See application file for complete search history.

(56) References Cited

U.S. PATENT DOCUMENTS

| 4,799,922 | A | 1/1989 | Beer et al. |
| 5,897,580 | A | 4/1999 | Silver |
| 5,941,847 | A * | 8/1999 | Huber ............... A61M 1/06 604/74 |
| 6,387,072 | B1 | 5/2002 | Larsson et al. |
| 6,723,066 | B2 | 4/2004 | Larsson et al. |
| 8,529,501 | B2 | 9/2013 | Wach et al. |
| 2002/0062103 | A1 | 5/2002 | Larsson et al. |
| 2002/0072702 | A1 * | 6/2002 | Quay ............... A61B 5/14546 604/74 |
| 2004/0074859 | A1 * | 4/2004 | Hanna .............. A61J 9/00 215/11.1 |
| 2004/0122356 | A1 * | 6/2004 | Burke ............... A61M 1/06 604/74 |
| 2006/0025718 | A1 * | 2/2006 | Ostrowski ........ A61J 9/00 604/74 |
| 2007/0173756 | A1 * | 7/2007 | Krebs ............... A61M 1/06 604/74 |
| 2011/0251552 | A1 * | 10/2011 | Brittner ........... A61M 1/06 604/74 |
| 2014/0236072 | A1 * | 8/2014 | Zhang .............. A61M 1/06 604/23 |

FOREIGN PATENT DOCUMENTS

| WO | 03068291 | 8/2003 |
| WO | WO 2013066919 A2 * | 5/2013 ........... A61M 1/06 |
| WO | 2013088310 | 6/2013 |
| WO | WO 2013/066919 A2 * | 10/2013 |

* cited by examiner

*Primary Examiner* — Kami A Bosworth
*Assistant Examiner* — Jenna Zhang
(74) *Attorney, Agent, or Firm* — Hartman & Citrin LLC

(57) ABSTRACT

Embodiments of a breast pump shield are disclosed herein. According to various embodiments, the breast pump shield can include a body portion that has a breast engagement portion and a throat portion. The breast engagement portion can include a ring. The breast engagement portion can receive at least a portion of a breast of a user, and the throat portion can be configured to receive at least a portion of a nipple of the user and to receive milk from the breast. The breast pump shield also can include a suction chamber located adjacent to the throat portion, and a cover located at the ring of the body portion. The cover can include a support layer and a lubricant layer. The cover can provide at least part of a hermetic seal for the breast pump shield prior to use.

20 Claims, 9 Drawing Sheets

BREAST PUMP SHIELD

TECHNICAL FIELD

This disclosure relates generally to breast pumps. More particularly, the disclosure made herein relates to a human breast pump shield that can be easy to use, comfortable to use, and can be formed as a disposable article for purposes of convenience, sanitation, and/or other reasons.

BACKGROUND

Unless otherwise indicated herein, the details in this section are not prior art to the claims in this application and are not admitted to be prior art by inclusion in this section.

Until the middle of the twentieth century, almost all children were breastfed by their mothers (or a substitute such as a wet nurse). From around the 1940's through the 1990's, the popularity and prevalence of breastfeeding decreased in the United States. In the late part of the twentieth century and over the past ten to fifteen years, breastfeeding has experienced somewhat of a revival in the United States, with medical experts encouraging mothers to breastfeed children based upon a large body of scientific evidence that breastfeeding encourages healthy growth and development of children.

In modern American society, however, many mothers work outside the home or are busy with various activities that often require them to leave their homes. For many mothers, this time away from the home can be disruptive to breastfeeding schedules. Some mothers employ breast pumps to pump or express breast milk at home, at the office, or elsewhere.

Because breast milk is consumed primarily by young children, first and foremost infants of zero to six months of age and secondarily children up to about two to four years of age, some experts encourage sterilization and frequent cleaning of breast pump components. When away from the home, mothers may experience difficulty in finding a suitable place and/or equipment to thoroughly clean the breast pump components. As such, breast pumping outside the home can be difficult for mothers.

Furthermore, some women experience pain during or after breast pumping. In particular, some women experience pain as the nipples enlarge during pumping and/or from rubbing that can occur during use of a breast pump. Various approaches are used in an attempt to reduce this pain. For example, some mothers use a low setting for a breast pump at the beginning of pumping and later, after the nipple has extended and/or enlarged, the suction and/or speed of the breast pump can be increased without causing pain to the mother.

Because some breast pumps do not have variable settings, and because many mothers want to complete breast pumping as quickly as possible when away from the home, some mothers are unable to address the pain that may occur during pumping. Because of this, some mothers are discouraged from breastfeeding their children or may cease breastfeeding at the earliest opportunity.

SUMMARY

Concepts and technologies are disclosed herein for a breast pump shield. As used herein, a "breast" is used to refer only to a breast of a human female and specifically excludes breasts of other living organisms. In some embodiments, a breast pump shield can be formed from a plastic or other material. The breast pump shield can include a body portion and one or more covers. The cover can include multiple layers. According to various embodiments, the cover includes three layers, a lubricant layer, a support layer, and a wiping layer. A layer of lubricant ("lubricant layer") also can be located within the body portion of the breast pump shield.

The lubricant layer can be included to reduce irritation associated with using the breast pump shield by lubricating surfaces that come into contact with the breasts of the user and/or portions of the breasts of the user. The lubricant can be formulated in a manner that prevents thinning and/or degradation of the lubricant in high heat environments. Furthermore, the cover can include a lubricant layer so that a user need not apply lubricant to the breasts and/or the breast pump shield prior to use.

The support layer can be provided to support the adhesive layer and the wiping layer, as well as to provide a hermetic seal for the breast pump shield. By providing a hermetic seal for the breast pump shield, the cover can ensure that the breast pump shield remains sterile, as well as preventing leakage of, oxidation of, and/or degradation of the lubricant layer located within the body portion. The wiping layer can be included to provide a wipe or cleaner for the user. The wiping layer can be removed from the other layers, in some embodiments, and can be used to clean up before, during, or after pumping.

According to some embodiments, the breast pump shield and/or components thereof can be formed from a rigid material such as an epoxy resin or other resins, plastics, thermoplastics, acrylics, rubber, synthetic rubber, other polymers or copolymers, combinations thereof, or the like. In some other embodiments, the breast pump shield and/or components thereof can be formed from semi-rigid and/or soft materials such as rubber, plastic films, latex, or the like. The soft material can be located within a frame or other support structures to provide rigidity for the breast pump shield. These and other embodiments of the concepts and technologies described herein will be illustrated and described herein.

According to one aspect of the concepts and technologies described herein, a breast pump shield is disclosed. The breast pump shield can include a body portion. The body portion can include a breast engagement portion and a throat portion. The breast engagement portion can include a ring. The breast engagement portion can receive at least a portion of a breast of a user. The throat portion can be configured to receive at least a portion of a nipple of the user and to receive milk from the breast. The breast pump shield also can include a suction chamber. The suction chamber can be located adjacent to the throat portion. The breast pump shield also can include a cover located at the ring of the body portion. The cover can include a support layer and a lubricant layer, and the cover can provide at least part of a hermetic seal for the breast pump shield prior to use.

In some embodiments, the lubricant layer can include a layer of food grade lubricant. The food grade lubricant can include at least one lubricant selected from a group that includes a nut-based lubricant, a coconut-based lubricant, and a vegetable-based lubricant. In some embodiments, the lubricant layer can include a layer of lubricant. The lubricant can include at least one lubricant selected from a group that includes a mineral-oil based lubricant, a petroleum-based lubricant, and a shea-based lubricant.

In some embodiments, the cover further can include a wiping layer. The wiping layer can be formed from a cotton-based fabric. In some embodiments, a further lubricant layer can be located within the body portion, the throat portion, and the suction chamber, and a further cover can be located over an inlet formed in the suction chamber. In some embodiments, the support layer can be formed from a metal foil. The support layer can prevent leakage of the lubricant layer from the breast pump shield.

In some embodiments, the body portion can be formed from a semi-rigid material. The body portion further can include support surfaces and rods to provide the body portion with rigidity. In some embodiments, the throat portion can include a ridged portion that collapses and expands. In some embodiments, the breast pump shield can include support surfaces and rods that can be used to provide rigidity for the ridged portion and to prevent collapsing of the ridged portion during use of the breast pump shield.

According to another aspect of the concepts and technologies described herein, a breast pump shield is disclosed. The breast pump shield can include a body portion that includes a breast engagement portion and a throat portion. The breast engagement portion can include a ring. The breast engagement portion can receive at least a portion of a breast of a user, and the throat portion can be configured to receive at least a portion of a nipple of the user and to receive milk from a human breast. The breast pump shield also can include a suction chamber located adjacent to the throat portion. The suction chamber can include an inlet. The breast pump shield also can include a cover located at the ring of the body portion. The cover can include a support layer, a lubricant layer located adjacent to a first side of the support layer, and a wiping layer located adjacent to a second side of the support layer. The cover can provide at least part of a hermetic seal for the breast pump shield prior to use. When the breast pump shield is used, the cover can be removed, thereby destroying the hermetic seal.

In some embodiments, the lubricant layer can include a layer of food grade lubricant. The food grade lubricant can include at least one lubricant selected from the group that includes a nut-based lubricant, a coconut-based lubricant, a flax-seed-based lubricant, a fish-oil-based lubricant, and a vegetable-based lubricant. The lubricant layer also can include a layer of lubricant selected from a group of lubricants that includes a mineral-oil based lubricant, a petroleum-based lubricant, and a shea-based lubricant.

In some embodiments, a further lubricant layer can be located within the body portion, the throat portion, and the suction chamber, and a further cover can be located over an inlet formed in the suction chamber. In some embodiments, the breast pump shield also includes an assembly structure for connecting the breast pump shield to a bottle, and another cover located at the assembly structure. In some embodiments, the throat portion can include a ridged portion that collapses and expands.

According to yet another aspect of the concepts and technologies described herein, a breast pump shield is disclosed. The breast pump shield can include a body portion. The body portion can include a breast engagement portion and a throat portion. The breast engagement portion can include a ring. The breast engagement portion can receive at least a portion of a breast of a user. The throat portion can be configured to receive at least a portion of a nipple of the user and to receive milk from a human breast. The breast pump shield also can include a suction chamber located adjacent to the throat portion. The suction chamber can include an inlet through which a breast pump is connected to the suction chamber. The breast pump shield also can include a cover located at the ring of the body portion. The cover can include a support layer, a lubricant layer located adjacent to a first side of the support layer, and a wiping layer located adjacent to a second side of the support layer. The cover can provide at least part of a hermetic seal for the breast pump shield prior to use.

In some embodiments, a further lubricant layer can be located within the body portion, the throat portion, and the suction chamber. A further cover can be located over an inlet formed in the suction chamber. In some embodiments, the lubricant layer can include a layer of lubricant selected from a group of lubricants that includes a nut-based lubricant, a coconut-based lubricant, a flax-seed-based lubricant, a fish-oil-based lubricant, a vegetable-based lubricant, a mineral-oil based lubricant, a petroleum-based lubricant, and a shea-based lubricant.

The foregoing summary is illustrative only and is not in any way limiting. In addition to the illustrative aspects, embodiments, and features described above, further aspects, embodiments, and features will become apparent by reference to the drawings and the following detailed description.

DETAILED DESCRIPTION

Figure 1:
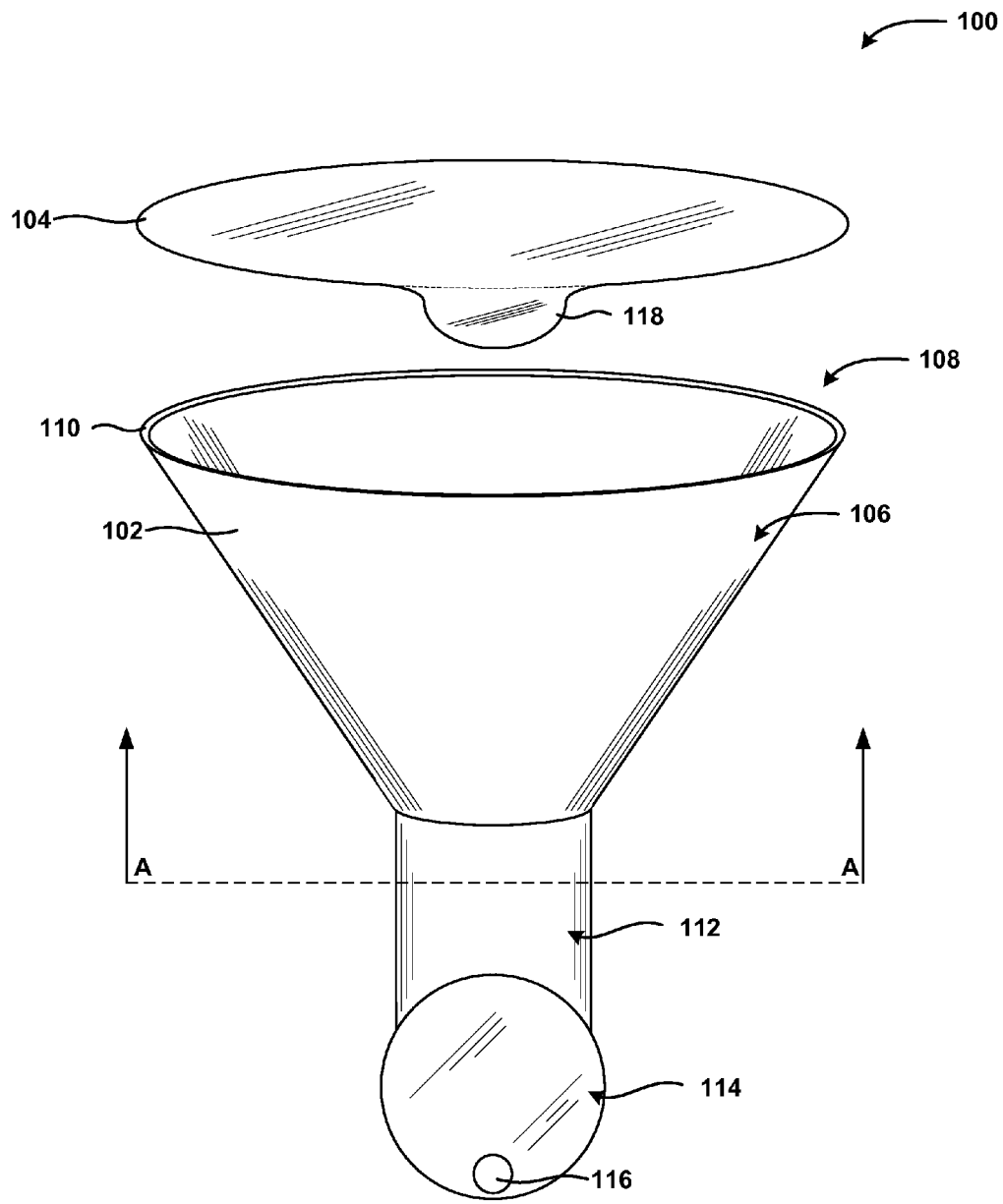
FIG. 1 is line drawing showing a top elevation view of a breast pump shield, according to an illustrative embodiment of the concepts and technologies described herein.

The following detailed description is directed to a breast pump shield. In some embodiments a breast pump shield can be formed from a plastic or other material. The breast pump shield can include a body portion and one or more covers. At least one of the one or more covers can include multiple layers. According to various embodiments, at least one of the covers includes three layers, namely a lubricant layer, a support layer, and a wiping layer. A layer of lubricant ("lubricant layer") also can be located within the body portion of the breast pump shield.

The lubricant layer can be included to reduce irritation associated with using the breast pump shield by lubricating surfaces that come into contact with the breasts of the user and/or portions of the breasts of the user. The lubricant can be formulated in a manner that prevents thinning and/or degradation of the lubricant in high heat environments. Furthermore, the cover can include a lubricant layer so that a user need not apply lubricant to the breasts and/or the breast pump shield prior to use, or so that the user can have extra lubricant if needed or desired. In some embodiments, the lubricant layer is included as a packet of lubricant attached to the cover, wherein a user can squeeze the cover after removing the cover from the breast pump shield, thereby ejecting the lubricant from the lubricant layer for placement on the breast, areola, nipple, shield, or other structure or body part.

The support layer can be provided to support the adhesive layer and the wiping layer, as well as to provide a hermetic seal for the breast pump shield. By providing a hermetic seal for the breast pump shield, the cover can ensure that the breast pump shield remains sterile, as well as preventing leakage of, oxidation of, and/or degradation of the lubricant layer located within the body portion. The wiping layer can be included to provide a wipe or cleaner for the user. The wiping layer can be removed from the other layers, in some embodiments, and can be used to clean up before, during, or after pumping.

According to some embodiments, the breast pump shield and/or components thereof can be formed from a rigid material such as an epoxy resin or other resins, plastics, thermoplastics, acrylics, rubber, synthetic rubber, other polymers or copolymers, combinations thereof, or the like. In some other embodiments, the breast pump shield and/or components thereof can be formed from semi-rigid and/or soft materials such as rubber, plastic films, latex, or the like. The soft material can be located within a frame or other support structures to provide rigidity for the breast pump shield. These and other embodiments of the concepts and technologies described herein will be illustrated and described herein. These and other aspects of the concepts and technologies described herein will be described herein in further detail.

In the following detailed description, references are made to the accompanying drawings that form a part hereof, and in which are shown by way of illustration specific embodiments or examples. It must be understood that the disclosed embodiments are merely illustrative of the concepts and technologies disclosed herein. The concepts and technologies disclosed herein may be embodied in various and alternative forms, and/or in various combinations of the embodiments disclosed herein. The word "illustrative," as used in the specification, is used expansively to refer to embodiments that serve as an illustration, specimen, model or pattern.

Additionally, it should be understood that the drawings are not necessarily to scale, and that some features may be exaggerated or minimized to show details of particular components. In other instances, well-known components, systems, materials or methods have not been described in detail in order to avoid obscuring the present disclosure. Therefore, specific structural and functional details disclosed herein are not to be interpreted as limiting, but merely as a basis for the claims and as a representative basis for teaching one skilled in the art to variously employ the present disclosure. Referring now to the drawings, in which like numerals represent like elements throughout the several figures, aspects of breast pump shields will be presented.

Referring first to FIG. 1, aspects of a breast pump shield 100 according to various embodiments of the concepts and technologies described herein will be described in detail. In particular, FIG. 1 illustrates one illustrative embodiment of a breast pump shield 100. It should be understood that the illustrated and described illustrative embodiment of the breast pump shield 100 shown in FIG. 1 is one illustrative embodiment of the concepts and technologies described herein, and therefore should not be construed as being limiting in any way of the concepts and technologies described herein.

In some embodiments, as shown in FIG. 1, a breast pump shield 100 can include a breast pump shield main body portion ("body portion") 102 and a cover 104. The body portion 102 can be configured to engage a breast during lactation. The body portion 102 also can be configured to support other components of the breast pump shield 100. As will be illustrated and described in more detail below, the body portion 102 can have various configurations and/or features. As such, the illustrated and described example embodiment shown in FIG. 1 is merely illustrative of the concepts and technologies described herein and should not be construed as being limiting in any way.

The body portion 102 can include various components. In some embodiments, the body portion 102 can include a breast engagement portion 106. The breast engagement portion 106 can be configured to receive and/or engage an outer surface of a breast of a user. The breast engagement portion 106 also can be configured to center a nipple of the breast within the breast engagement portion 106 during lactation/suction and/or to encourage the nipple of the breast to enter a suction and/or stimulation chamber, as will be explained in more detail below.

According to various embodiments, a breast or a portion thereof can be inserted into the breast engagement portion 106 via an open end 108. The open end 108 can be defined, in some embodiments, by a ring 110 of material located at the open end 108. The ring 110 can engage the breast or chest of the user and the breast or areola of the user can be engaged within the breast engagement portion 106, or a portion thereof. The nipple of the breast can pass through the breast engagement portion 106 and into a stimulation and/or suction chamber or region. In the illustrated embodiment, the stimulation chamber or region is provided by a throat portion 112 of the body portion 102. It should be understood that this example is illustrative and therefore should not be construed as being limiting in any way.

The throat portion 112 can be configured to accommodate and/or engage the nipple during lactation. In various embodiments, the throat portion 112 can be configured as a cylindrical passageway. The throat portion 112 can be tapered, in some embodiments, though this is not necessarily the case. During pumping, the nipple can extend to or even into the throat portion 112.

According to various embodiments, the extension of the nipple into, through, or within the throat portion 112 can occur repeatedly with the application of suction to the throat portion. The movement and/or extension of the nipple within the throat portion 102 can encourage and/or stimulate milk flow, as generally is understood. The body portion 102 also can include a suction chamber, structure, or region ("suction chamber") 114. Air pressure within the suction chamber 114 can be controlled and/or regulated by a breast pump (not visible in FIG. 1), which can be connected to the suction chamber 114 via a hose, connector, or other structure. The hose, connector, or other structure can be connected to or inserted into the suction chamber 114 via an inlet 116. Thus, the breast pump or other device can control air pressure within the suction chamber 114, the throat portion 112, and/or the breast engagement portion 106 via connection through the inlet 116. It should be understood that this example is illustrative and therefore should not be construed as being limiting in any way.

According to various embodiments, the body portion 102 and/or one or more portions thereof can include a lubricant layer (not visible in FIG. 1). In the illustrated embodiment, at least portions of the breast engagement portion 106 and the throat portion 112 include the lubricant layer. In some embodiments, the suction chamber 114, the inlet 116, other portions of the breast pump shield 100 and/or portions thereof can include the lubricant layer. The lubricant layer will be illustrated and described in more detail below, particularly with reference to FIGS. 3-4B. Additionally, the cover 104 will be illustrated and described in more detail below.

Components of the breast pump shield 100 can be formed from various materials. According to various embodiments, the body portion 102 of the breast pump shield 100 and/or components of the body portion 102 such as the breast engagement portion 106, the ring 110, the throat portion 112, and/or the suction chamber 114 can be formed from one or more plastics, one or more thermoplastics, one or more acrylics, one or more resins, one or more polymers or copolymers, other (non-plastic and non-polymer) materials, and/or combinations thereof. According to some embodiments, the body portion 102 of the breast pump shield 100 can be formed using various manufacturing processes such as injection molding processes, three dimensional printing processes, machining processes, forging processes, combinations thereof, or the like. Because other materials and/or processes can be used to form the body portion 102 and/or other components of the breast pump shield 100, it should be understood that these examples are illustrative and therefore should not be construed as being limiting in any way.

In some embodiments, as can be seen in FIG. 1, the cover 104 can include a finger grip, tab, protrusion, or other structure ("tab") 118. The tab 118 can be used to provide a grip for a user to grasp the cover 104. Using the tab 118, the user can detach the cover 104 from the breast pump shield 100. It can be appreciated that in various embodiments, the cover 104 can be attached to the breast pump shield 100 using an adhesive. Thus, the cover 104 can be peeled away from the breast pump shield 100, in some embodiments, as generally is understood. Because the tab 118 can be optional and/or can be replaced by additional and/or alternative structures or devices, the tab 118 is not shown in the other FIGURES. It should be understood that the tab 118 or other structures or devices can be included in some, all, or none of the illustrated embodiments, and as such, the illustrated embodiments that omit the tab 118 are merely illustrative and should not be construed as being limiting in any way.

In some embodiments, the cover 104 can be configured such that the cover can enwrap the entire breast pump shield 100 or a component thereof. For example, in some embodiments, the cover 104 can enwrap the entire breast pump shield 100, the entire body portion 102, the entire throat portion 112, and/or other components of the breast pump shield 100. In some embodiments, the components of the breast pump shield 100 can be enwrapped or enclosed by the cover 104 and/or multiple covers 104, so a user can unwrap the components and assembly the sterile and lubricated components together. In some other embodiments, the entire breast pump shield 100 can be unwrapped, and then can be used as a sterile and lubricated breast pump shield. Thus, the embodiments shown in the FIGURES, wherein the cover 104 covers only a portion of the breast pump shield 100 should be understood as being illustrative of some contemplated embodiments and should not be construed as being limiting in any way.

The breast pump shield 100 shown in FIG. 1 has been described as including one cover 104, one breast engagement portion 106, one throat portion 112, one suction chamber 114, and one inlet 116. It should be understood, however, that some embodiments of the breast pump shield 100 can include zero, one, or more than one cover 104, zero, one, or more than one breast engagement portion 106, zero, one, or more than one throat portion 112, zero, one, or more than one suction chamber 114, and/or zero, one, or more than one inlet 116. In one contemplated embodiment, for example, the breast pump shield 100 can include a truncated breast engagement portion or can omit the breast engagement portion 106 altogether, thereby resulting in a short and compact breast pump shield 100 that essentially consists of the throat portion 112 and the suction chamber 114. It should be understood that this example is illustrative and therefore should not be construed as being limiting in any way.

Figure 2A:
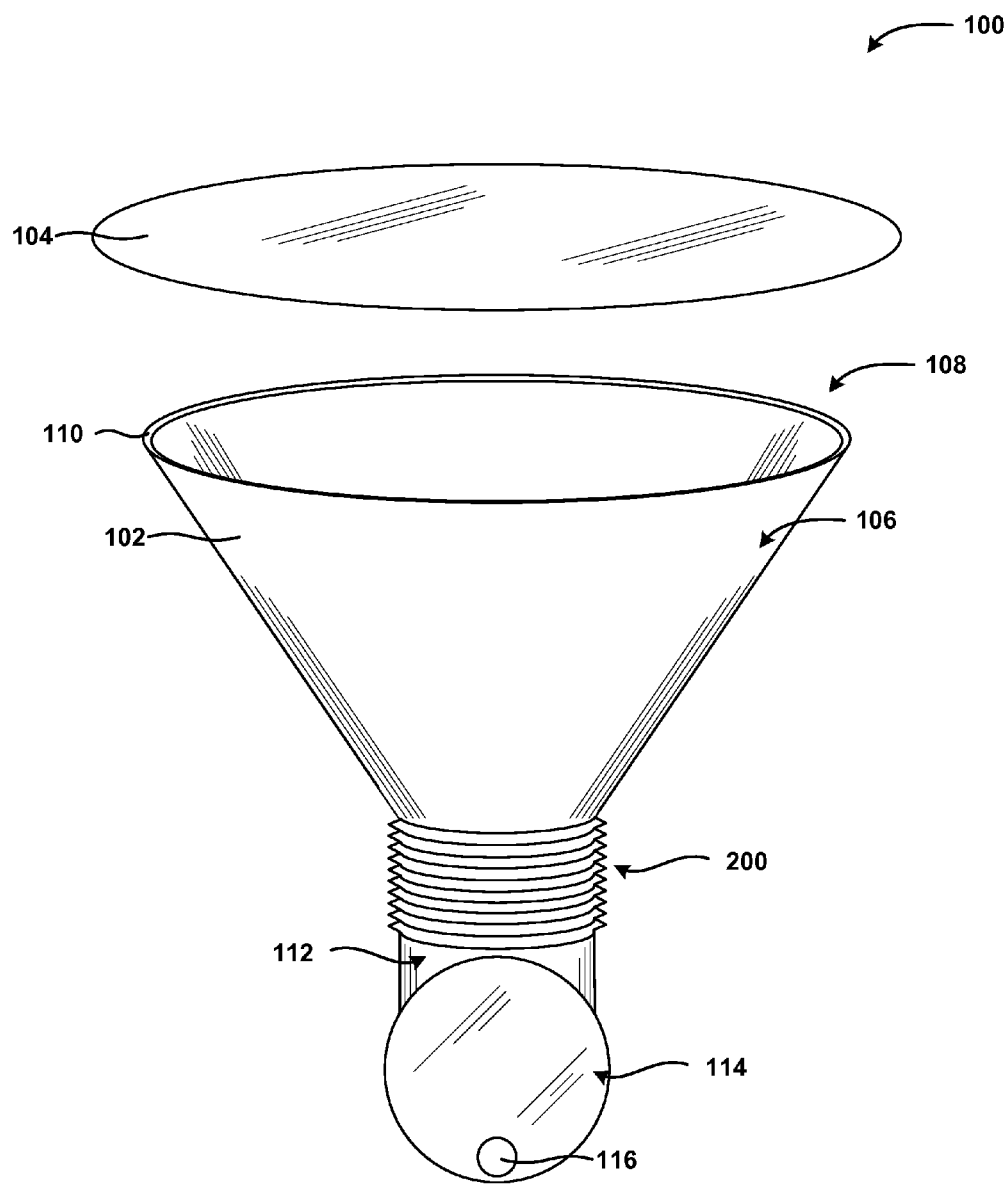
FIGS. 2A-2B are line drawings illustrating top elevation views of a breast pump shield, according to another illustrative embodiment of the concepts and technologies described herein.
Figure 2B:
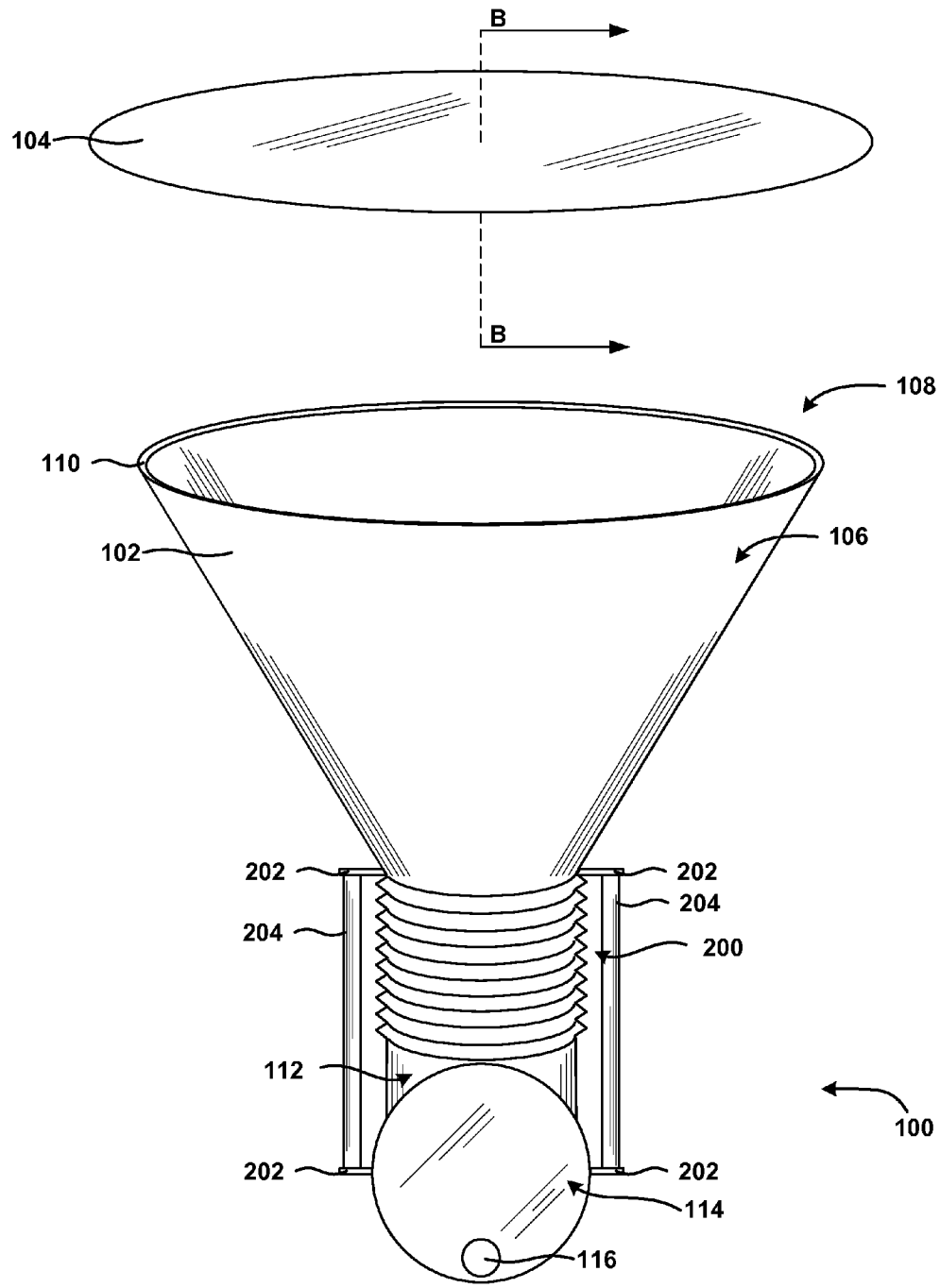

Turning to FIGS. 2A-2B, additional details of the breast pump shield 100 are illustrated and described in detail. In particular, FIGS. 2A-2B are line drawings illustrating top elevation views of a breast pump shield, according to another illustrative embodiment of the concepts and technologies described herein. Because the various components of the breast pump shield 100 can be arranged in various configurations, it should be understood that the views shown in FIGS. 2A-2B could also correspond to side elevation views and/or bottom elevation views instead of, or in addition to, top elevation views.

As shown in FIG. 2A, some embodiments of the breast pump shield 100 can include an expandable and/or collapsible throat portion 112. In various embodiments, the expandable and/or collapsible throat portion 112 can include an expandable and collapsible ridged portion (hereinafter referred to as a "ridged portion") 200. The ridged portion 200 can be collapsed or expanded based on desires or needs of a user. In the embodiment shown in FIG. 2A, the ridged portion 200 of the throat portion 112 is illustrated as being collapsed, while in FIG. 2B, ridged portion 200 of the throat portion 112 is illustrated as being expanded. It should be understood that these examples are illustrative and therefore should not be construed as being limiting in any way.

In some embodiments, the ridged portion 200 can be included on the breast pump shield 100 to collapse the breast pump shield 100, at least partially, to make the size of the breast pump shield 100 compact. Thus, when the ridged portion 200 is collapsed, the breast pump shield 100 may consume less space in a diaper bag, glove compartment, purse, or other area for convenience. In some embodiments, the ridged portion 200 also can be used to protect the lubricant layer. In particular, the ridges of the ridged portion 200 can be used to hold or retain the lubricant used to provide the lubricant layer at a desired location. It should be understood that this example is illustrative and therefore should not be construed as being limiting in any way.

In some embodiments, an example of which is shown in FIG. 2B, the breast pump shield 100 can include support structures such as the supports 202 and the support rods 204. According to various embodiments, the supports 202 and/or the rods 204 can be formed from plastics, metals, alloys, thermoplastics, acrylics, epoxies and/or resins, wood, glass, and/or other materials. The support structures can be used to hold the breast pump shield 100 in a configuration at which the ridged portion 200 is expanded. It can be appreciated that the suction generated by the breast pump (whether manual or electronic) can be sufficient to collapse the ridged portion 200, which can reduce the realized suction at the nipples of the user. Thus, some embodiments such as the example shown in FIG. 2B include the support structures. In some embodiments, the rods 204 can be removable and/or reusable. As such, the rods 204 can be removed, and the ridged portion 200 can be collapsed, if desired.

Although not visible in the FIGURES, some embodiments of the concepts and technologies described herein include additional supports 202 and rods 204. In particular, supports can be located near the ring 110 and near the bottom of the breast engagement portion 106 (near the beginning of the throat portion 112). Thus, some embodiments of the concepts and technologies described herein can make use of collapsible and/or soft or semi-soft materials for the body portion 102. A collapsible or semi-collapsible body portion 102 can be provided with support by the supports 202 and rods 204. It should be understood that these examples are illustrative and therefore should not be construed as being limiting in any way.

Figure 3:
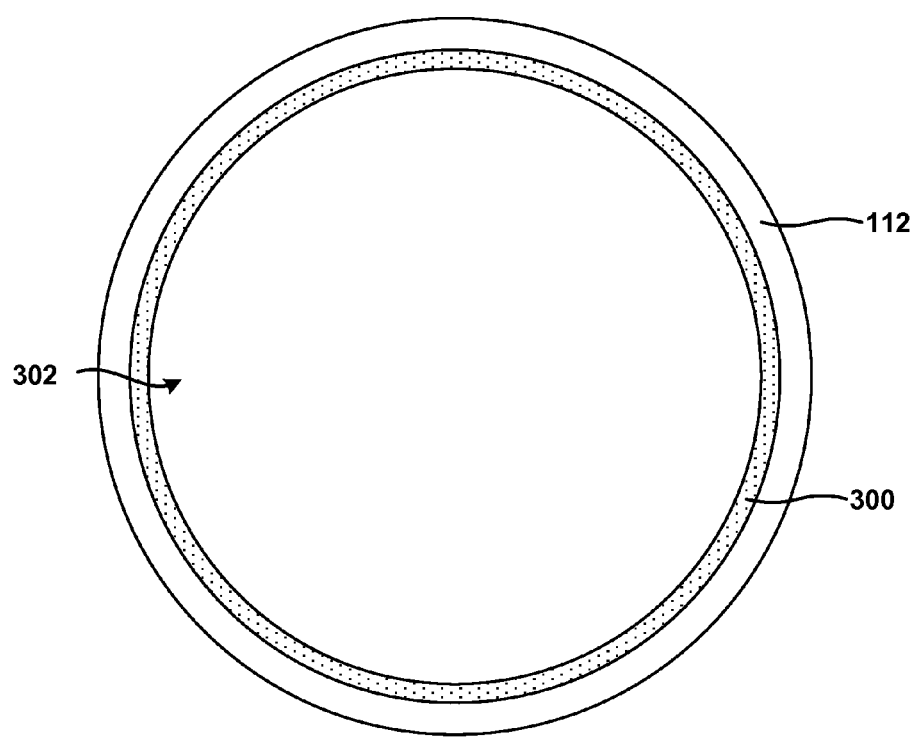
FIG. 3 is a line drawing illustrating additional features of a breast pump shield, according to some illustrative embodiments of the concepts and technologies described herein.

Turning now to FIG. 3, additional aspects of the concepts and technologies described herein for a breast pump shield will be described in detail. In particular, FIG. 3 is a line drawing illustrating cut-away view of the throat portion 112 of the breast pump shield 100 as viewed from the cut-line A-A shown in FIG. 1, according to some illustrative embodiments of the concepts and technologies described herein. It should be understood that this example is illustrative and therefore should not be construed as being limiting in any way.

As can be seen in FIG. 3, the throat portion 112 can include a lubricant layer 300 disposed within the throat portion 112. In some embodiments, the lubricant layer 300 can be located between an inner surface (not labeled in FIG. 3) of the throat portion 112 and a void 302 of the throat portion 112. As mentioned above, it can be appreciated that the void 302 can accommodate a nipple of a lactating mother during pumping and/or use of the breast pump shield 100. As such, in some embodiments the lubricant layer 300 can be included to lubricate the inner surface of the throat portion 112. The lubricant layer 300 can be included to prevent irritation of the nipples, which can result from pumping. Similarly, the lubricant layer 300 can be included to reduce pain, which some women may experience when pumping. Still further, the lubricant layer 300 can be included to allow the nipple to slide up and down along the side wall of the throat portion 112, which can stimulate the nipples and encourage milk flow. It should be understood that these examples are illustrative and therefore should not be construed as being limiting in any way.

The functionality of the lubricant layer 300 can be provided, in some embodiments, by a food grade and/or hypoallergenic lubricant. Thus, the lubricant layer 300 can be safe for use during lactation as any amounts (trace or otherwise) that pass into the expressed or pumped breast milk may not pose a risk to an infant, toddler, or other child or children who consume the milk produced using the breast pump shield 100. According to one contemplated embodiment, the lubricant used to provide the lubricant layer 300 can include a coconut-based lubricant. According to another contemplated embodiment, the lubricant used to provide the lubricant layer 300 can include a palm-based lubricant. According to another embodiment, the lubricant used to provide the lubricant layer 300 can include a fruit-based or vegetable-based lubricant such an olive-oil-based lubricant, a vegetable-oil-based lubricant (e.g., canola oil, soy oil, peanut oil, corn oil, avocado oil, safflower oil, sunflower oil, etc.), nut oils (e.g., almond oil, walnut oil), other oils (e.g., cottonseed oil, sunflower oil, etc.) combinations thereof, or the like. According to other embodiments, the lubricant used to provide the lubricant layer 300 can include other oils and/or lubricants such as petroleum based and/or mineral-based lubricants. According to still other embodiments, the lubricant used to provide the lubricant layer 300 can include flax oil or fish oil, which can be high in Omega-3 fatty acids that are known to encourage healthy brain development of infants. Thus, oil that leaks into the milk can actually be beneficial for the infant, in some embodiments. Because other oils and/or lubricants can be used, it should be understood that the above examples are illustrative and therefore should not be construed as being limiting in any way.

According to various embodiments, the lubricant layer 300 can be provided by a thick heat-resistant lubricant. As such, during shipping and/or other transportation of the breast pump shield 100, the lubricant layer 300 may not move or run. This functionality can be particularly useful when shipping the breast pump shield 100 in a high heat environment, or the like. As such, the breast pump shield 100 can be ready for use without applying lubricant to the breast pump shield 100, a component thereof, and/or a nipple or breast of the lactating mother. In some embodiments, the lubricant or oil used to provide the lubricant layer 300 can be thickened using various processes to prevent running and/or melting of the lubricant. It should be understood that this example is illustrative and therefore should not be construed as being limiting in any way.

Figure 4A:
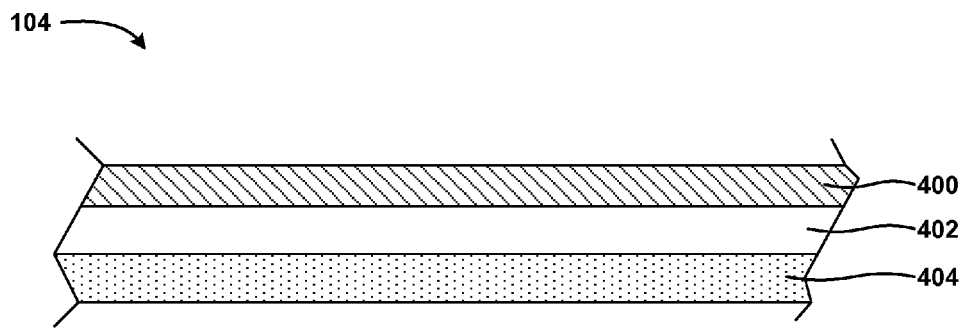
FIG. 4A is a line drawing illustrating some features of a breast pump shield cover, according to some illustrative embodiments of the concepts and technologies described herein.
Figure 4B:
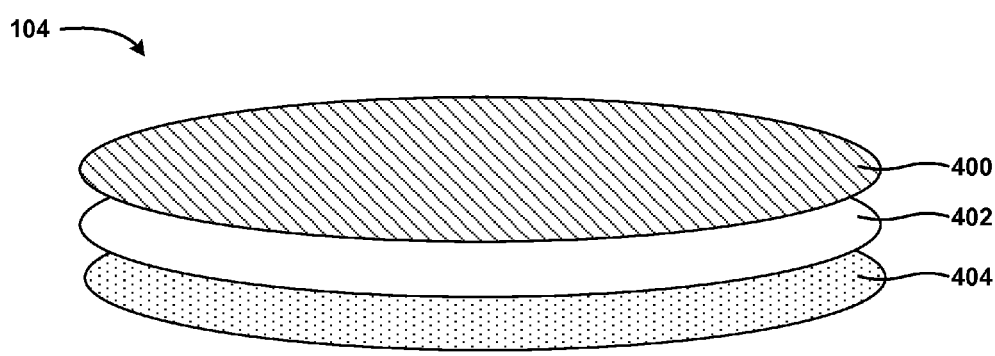
FIG. 4B is an assembly drawing of a breast pump shield cover, according to an illustrative embodiment of the concepts and technologies described herein.

Referring now to FIGS. 4A-4B, additional aspects of the concepts and technologies described herein for a breast pump shield 100 will be described in detail. In particular, FIG. 4A illustrates a cross section of the cover 104, viewed along the cut/view line B-B shown in FIG. 2B. It can be appreciated that a cross section view of any portion of the cover 104 can be substantially similar to the view shown in FIG. 4A. Additionally, FIG. 4B illustrates an assembly drawing of the cover 104. Collective reference will be made to FIGS. 4A-4B to describe the cover 104 and/or the components thereof.

As shown in FIGS. 4A-4B, the cover 104 can include multiple layers. According to various embodiments of the concepts and technologies described herein, the cover 104 can include two or more layers. According to some other embodiments, the cover 104 can include three or more layers. In the illustrated embodiment, the cover 104 includes three layers. Based upon the foregoing, it can be appreciated that the illustrated embodiment is illustrative and therefore should not be construed as being limiting in any way.

The cover 104 shown in FIGS. 4A-4B includes a wiping layer 400, a support layer 402, and a lubricant layer 404. According to various embodiments, the lubricant layer 404 can be provided by a lubricant that may be similar or even identical to the lubricant layer 300 illustrated and described above with reference to FIG. 3, though this is not necessarily the case. Thus, it can be appreciated that according to some embodiments of the concepts and technologies described herein, the lubricant layer 404 can be provided by a coconut-based lubricant, a palm-based lubricant, a shea-based lubricant, a petroleum-based lubricant, a nut-based lubricant, a fruit-based lubricant, a vegetable-based lubricant, a mineral-oil-based lubricant, other oils and/or lubricants, combinations thereof, or the like. Because the lubricant layer 404 can be provided by other lubricants, it should be understood that the above examples are illustrative and therefore should not be construed as being limiting in any way.

In some embodiments, the lubricant layer 404 can be thickened as explained above with reference to the lubricant layer 300. The lubricant layer 404 can be applied by a user to her nipples, areolas, and/or other parts of her breast to reduce friction, rubbing, and/or pain associated with pumping the breasts during milk production. As noted above, the lubricant layer 300 can be included to obviate the user from needing additional lubricant. As such, it can be appreciated that the lubricant layer 404 can be included to provide extra lubricant that may or may not be used by a user. In still other embodiments, the cover 104 can include the lubricant layer 404 so a user can rub the cover on the breasts and/or parts of the breast or on the breast pump shield 100 and/or components thereof to further lubricate the breasts and/or breast pump shield 100 as described herein. It should be understood that this example is illustrative and therefore should not be construed as being limiting in any way.

The support layer 402 can be provided to add strength and/or support to the cover 104, in some embodiments. In particular, in some embodiments, the support layer 402 can be provided by a layer, sheet, or piece of a metal foil, a plastic sheet, a polymer layer, and/or another substrate or material. In addition and/or instead of providing rigidity and/or support for the cover 104, the support layer 402 can, in some embodiments, provide a hermetic seal for the breast pump shield 100 to keep the breast pump shield sanitary and/or sterile. The support layer 402 also can be configured to prevent leakage of, oxidation of, and/or other degradation of the lubricant layer 300 and/or the lubricant layer 404 illustrated and described herein. In one contemplated embodiment, the support layer 402 is provided by a metal foil layer. It should be understood that this example is illustrative and therefore should not be construed as being limiting in any way.

According to some embodiments, the wiping layer 400 can be provided by a natural or synthetic fiber cloth layer. In particular, some embodiments of the wiping layer 400 include a cotton fiber layer, while some other embodiments of the wiping layer 400 are provided by synthetic fiber layer. The wiping layer 400 can be included for the convenience of the user.

In particular, the wiping layer 400 can be used as a napkin, towel, or the like, for cleaning the breast before, during, or after pumping. For example, the wiping layer 400 can be used to wipe lubricant off of the breast, to wipe milk off of the breast, to clean hands, fingers, or the like, and/or to wipe or clean other surfaces. In some contemplated embodiments, the wiping layer 400 can be joined to the support layer 402 using an adhesive. As such, in some embodiments a user can peel the wiping layer away from the support layer 402. It can be appreciated that the support layer 402 can prevent the wiping layer 400 from absorbing and/or touching the lubricant layer 404. It should be understood that these examples are illustrative and therefore should not be construed as being limiting in any way.

It can be appreciated from the above description of the cover 104 that the breast pump shield 100 can be ready for use. Thus, some embodiments of the concepts and technologies described herein are used to provide a disposable and/or travel breast pump shield 100 that does not require cleaning prior to use for pumping. Furthermore, embodiments of the concepts and technologies described herein provide a sterile and ready to use breast pump shield that requires no additional cleaning and/or lubrication prior to or after use, thereby providing a truly portable and/or disposable breast pump shield 100. It should be understood that these examples are illustrative and therefore should not be construed as being limiting in any way.

Although not visible in the FIGURES, it should be understood that the cover 104 and/or other covers for the breast pump shield 100 can include an adhesive layer. The adhesive layer can be disposed on the support layer 402 and/or on other layers or portions of the cover 104. In some contemplated embodiments, the adhesive is disposed about a ring of the support layer 402. In some embodiments, the adhesive can be disposed in a ring that substantially corresponds to a location of the ring 110 shown in FIG. 1. In some embodiments, the lubricant layer 404 does not extend to or onto the adhesive layer. Thus, the lubricant layer 404 can be configured not to interfere with the adhesive layer, in some embodiments. In some embodiments, the adhesive layer is releasable and/or re-sealable. Thus, some embodiments of the adhesive layer can allow the user to attach and/or detach the cover 104 from the breast pump shield 100. It should be understood that these examples are illustrative and therefore should not be construed as being limiting in any way.

Figure 5A:
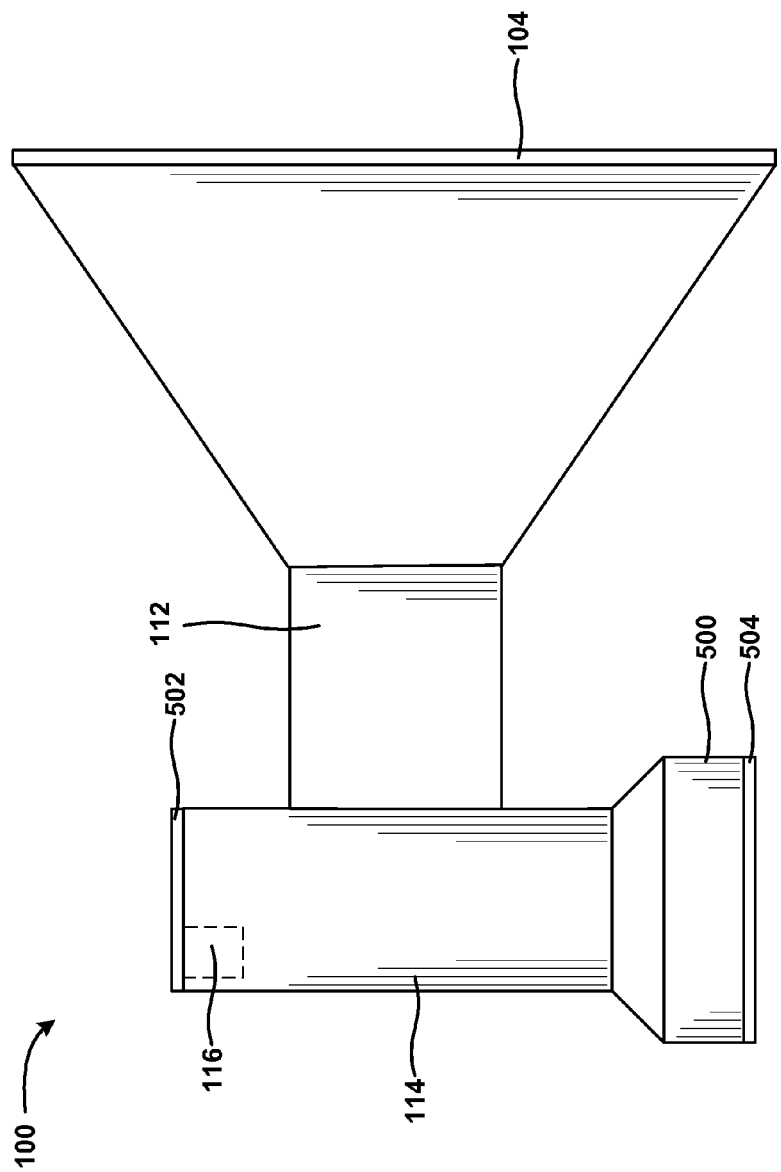
FIGS. 5A-5D are line drawings showing side elevation views of breast pump shields, according to some illustrative embodiments of the concepts and technologies described herein.

Turning now to FIGS. 5A-5D, additional aspects of the concepts and technologies described herein for a breast pump shield 100 will be described in detail. In particular, FIGS. 5A-5D illustrate side elevation views of several embodiments of the breast pump shield 100 illustrated and described herein. With reference to FIG. 5A, it can be appreciated that the breast pump shield 100 can include a bottle or container attachment assembly ("attachment assembly") 500. The attachment assembly 500 can be used to attach the breast pump shield 100 to a bottle or other container configured to receive and/or store milk produced during pumping.

Also visible in FIG. 5A, it can be seen that the suction chamber 114 can include a cover 502. The cover 502 can cover the inlet 116 and/or the suction chamber 114, though in various embodiments the suction chamber 114 is closed other than the inlet 116, and as such, the cover 502 can be included to cover the inlet 116. Although not visible in FIG. 5A, it should be understood that the cover 502 shown in FIG. 5A can include one or more layers including, but not limited to, the layers of the cover 104 illustrated and described herein. In the illustrated embodiment, the cover 502 includes a support layer and a lubricant layer.

In various embodiments, the lubricant layer of the cover 502 can be included to insure that the suction chamber 114 and/or the throat portion 112 are lubricated. The cover 502 also can be included to prevent lubricant from exiting the body portion 102 and/or components thereof. Still further, the cover 502 can be included to ensure that the breast pump shield 100 and/or components thereof remain sterile. In various embodiments, the cover 502 can cooperate with the cover 104 to provide at least part of a hermetic seal for the breast pump shield 100. In some embodiments, the cover 502 can include a wiping layer and/or other layers as illustrated and described above with reference to FIGS. 4A-4B, though this is not necessarily the case. As such, it should be understood that the examples illustrated and described herein with reference to FIGS. 5A-5D are illustrative and should not be construed as being limiting in any way.

As shown in FIG. 5A, the breast pump shield 100 also can include a cover 504. The cover 504 can be included to insure that the attachment assembly 500, the suction chamber 114, and/or the throat portion 112 are lubricated. The cover 504 also can be included to prevent lubricant from exiting the body portion 102 and/or components thereof. Still further, the cover 504 can be included to ensure that the breast pump shield 100 and/or components thereof remain sterile.

According to various embodiments, the cover 504 can cooperate with the cover 104 and the cover 502 to provide a hermetic seal for the breast pump shield 100. In some embodiments, the cover 504 can include a wiping layer and/or other layers as illustrated and described above with reference to FIGS. 4A-4B, though this is not necessarily the case. As such, it should be understood that the examples illustrated and described herein with reference to FIGS. 5A-5D are illustrative and should not be construed as being limiting in any way.

Figure 5B:
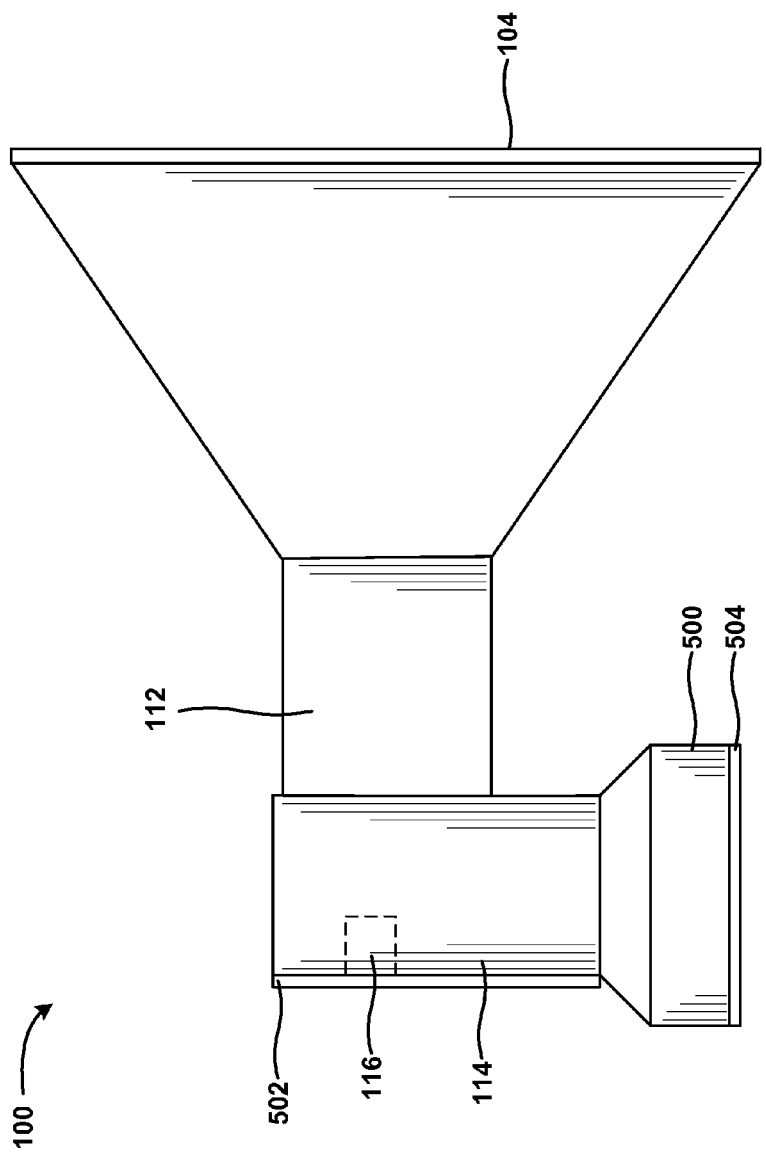

Turning to FIG. 5B, an additional embodiment of the concepts and technologies described herein are shown. As can be seen in FIG. 5B, the inlet 116 can be moved to various surfaces of the suction chamber 114 and/or the body portion 102. Correspondingly, the cover 502 can be located at various surfaces of the breast pump shield 100. Thus, it can be appreciated that the concepts and technologies described herein can be used with various configurations and/or shapes of breast pump shields without departing from the scope of this disclosure. It should be understood that this example is illustrative and therefore should not be construed as being limiting in any way.

Figure 5C:
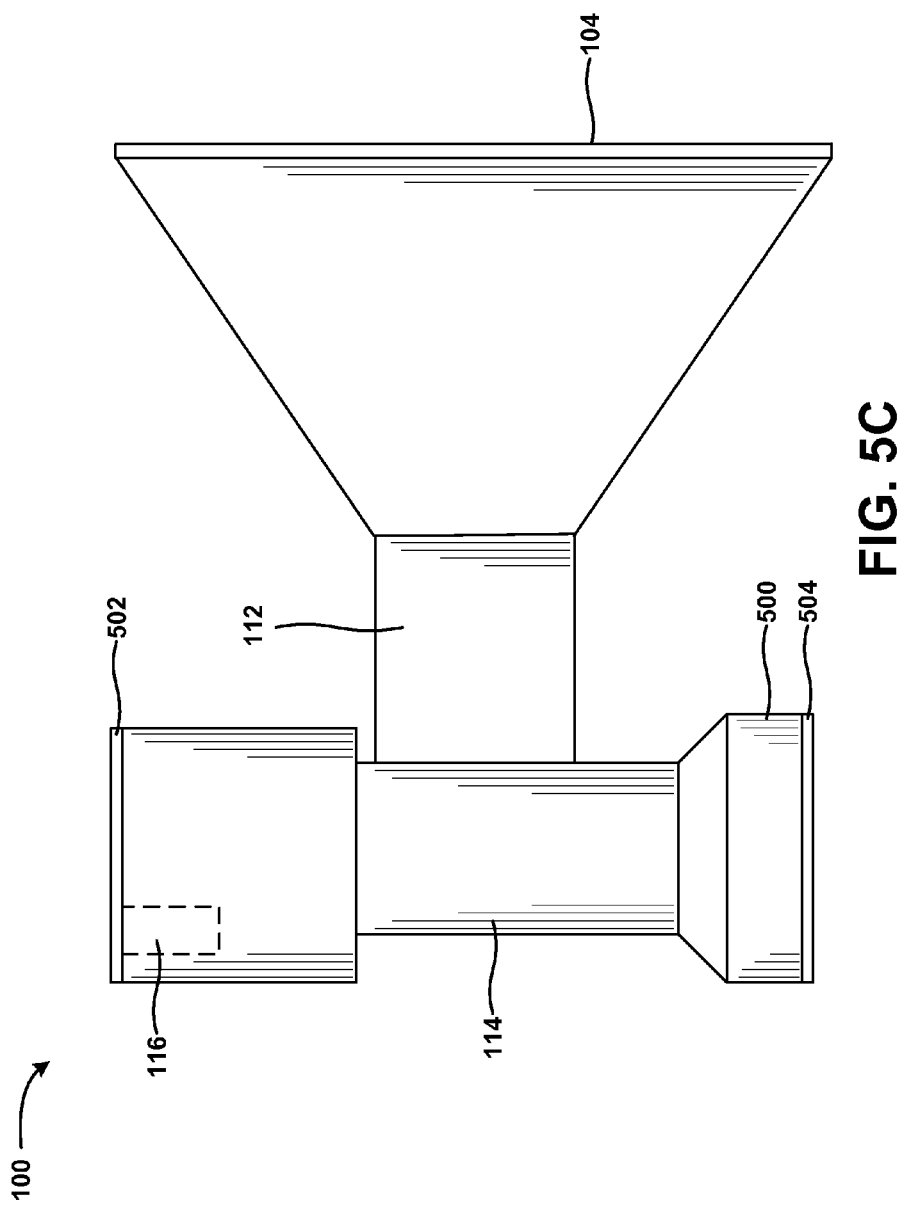

Turning to FIG. 5C, yet another embodiment of the concepts and technologies described herein are shown. As can be seen in FIG. 5C, the inlet 116 can be moved to yet another surface of the suction chamber 114 and/or other structures formed thereon and/or on the body portion 102. Correspondingly, the cover 502 can be located at various surfaces of the breast pump shield 100. Thus, it can be appreciated that the concepts and technologies described herein can be used with various configurations and/or shapes of breast pump shields without departing from the scope of this disclosure. It should be understood that this example is illustrative and therefore should not be construed as being limiting in any way.

Figure 5D:
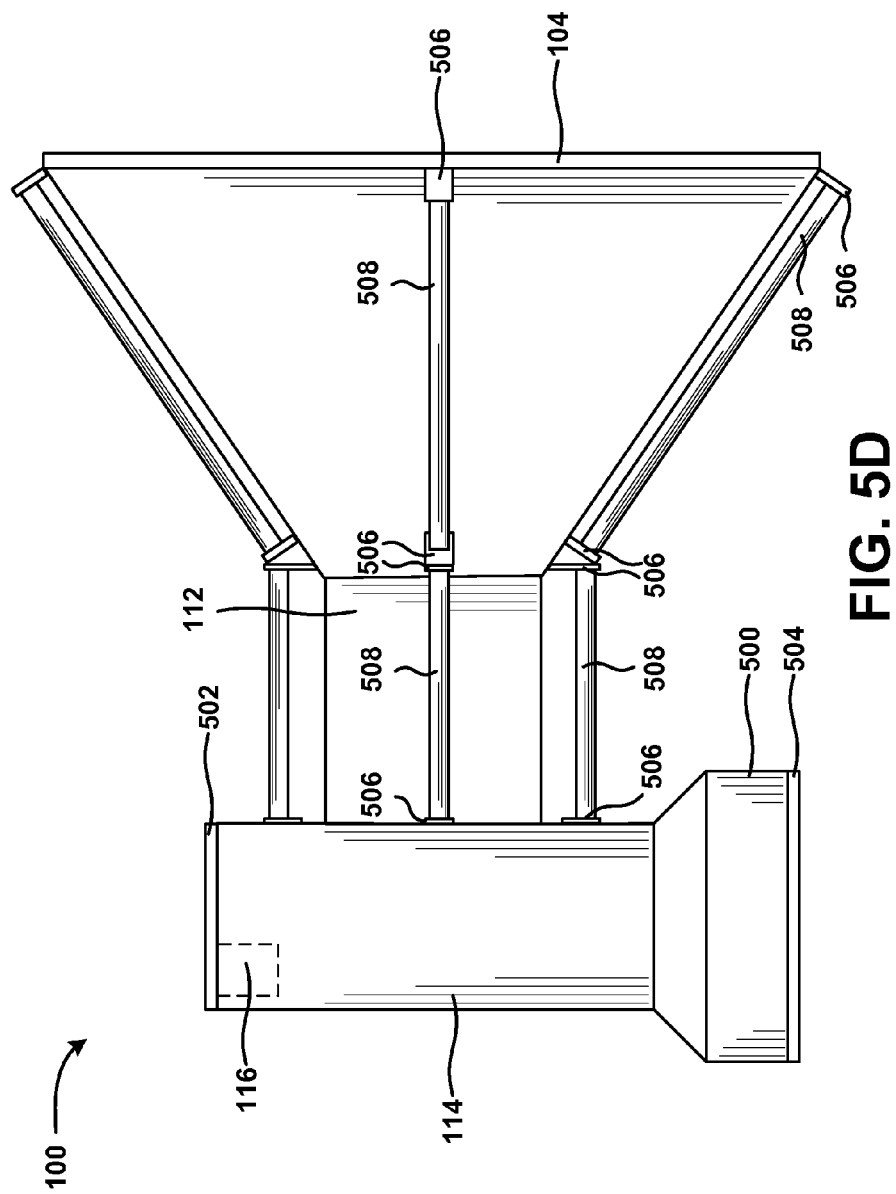

Turning now to FIG. 5D, another embodiment of the breast pump shield 100 is shown. In the embodiment shown in FIG. 5D, the breast pump shield 100 is formed from a soft or collapsible material such as a plastic, rubber, or polymer sheet, or the like. The body portion of the breast pump shield 100 can be held in shape and/or a proper configuration for pumping by way of various support structures 506, 508. It can be appreciated that the support structures 506, 508 can be removable, thereby allowing collapsing of the breast pump shield 100.

According to various embodiments, the support structures 506, 508 can include rings or support surfaces 506 formed on the body portion and rods 508 that can be placed between the rings or support surfaces 506 to provide the breast pump shield 100 with rigidity. The support structures 506, 508 can be reused and/or reusable, as these components do not need to be washed after pumping. It should be understood that these examples are illustrative and therefore should not be construed as being limiting in any way.

In practice, an embodiment of the breast pump shield 100 can be shipped with lubricant disposed within the breast pump shield 100. In some embodiments, the lubricant is disposed about the inner surfaces of the breast pump shield 100, while in some other embodiments, the lubricant layer can be provided by a packet of lubricant that can be squeezed by a user to eject the lubricant from the lubricant layer. Thus, a user can remove the cover 104 from the breast pump shield 100 prior to use, and either wipe the excess lubricant from the lubricant layer 404 of the cover 104 on the breast, areola, nipple, or other body part; wipe the excess lubricant from the lubricant layer 404 onto the breast pump shield and/or a component thereof, or discard of the cover 104. In some embodiments, the user can remove the wiping layer 400 of the cover 104 from the other layers for current or later use, or can leave the wiping layer 400 attached to the cover 104, depending upon user preference.

In some embodiments, wherein support structures are used, the user can locate the support structures in a proper configuration for use of the breast pump shield 100 and commence use of the breast pump shield 100. After use of the breast pump shield 100 to produce milk, the user can wipe her breasts and/or portions thereof with the wiping layer 400 of the cover 104 and dispose of the breast pump shield 100 without cleaning or otherwise maintaining the breast pump shield 100. In embodiments wherein the breast pump shield 100 includes support structures that are reusable, the user can remove the support structures from the breast pump shield 100 prior to disposing of the breast pump shield 100. It should be understood that these examples are illustrative and therefore should not be construed as being limiting in any way.

Based on the foregoing, it should be appreciated that embodiments of a breast pump shield have been disclosed herein. Although the subject matter presented herein has been described in conjunction with one or more particular embodiments and implementations, it is to be understood that the embodiments defined in the appended claims are not necessarily limited to the specific structure, configuration, or functionality described herein. Rather, the specific structure, configuration, and functionality are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the embodiments, which is set forth in the following claims.

I claim:

1. A breast pump shield comprising:
    a body portion comprising a breast engagement portion and a throat portion, wherein the breast engagement portion comprises a ring on an outer surface of the breast engagement portion, wherein the breast engagement portion is configured to receive least a portion of a human breast, and wherein the throat portion is configured to receive at least a portion of a nipple of the human breast and to receive milk from the human breast;
    a suction chamber located adjacent to the throat portion, the suction chamber comprising an inlet;
    a first cover located at the ring of the body portion, wherein the first cover comprises a support layer, a lubricant layer adjacent to a first side of the support layer, and a wiping layer adjacent to a second side of the support layer, wherein the first cover cooperates with the body portion to provide at least part of a hermetic seal for the breast pump shield prior to use;
    a further lubricant layer located within the body portion, the throat portion, and the suction chamber;
    a second cover located over the inlet formed in the suction chamber;
    an assembly structure configured to connect the breast pump shield to a bottle; and
    a third cover located at the assembly structure, wherein the support layer prevents leakage of the further lubricant layer from the breast pump shield.

2. The breast pump shield of claim 1, wherein at least one of the lubricant layer or the further lubricant layer comprises a layer of food grade lubricant.

3. The breast pump shield of claim 2, wherein the food grade lubricant comprises at least one lubricant selected from a group of lubricants consisting of:
    a coconut-based lubricant; and
    a vegetable-based lubricant.

4. The breast pump shield of claim 1, wherein the breast pump shield is disposable.

5. The breast pump shield of claim 1, wherein at least one of the lubricant layer or the further lubricant layer comprises at least one lubricant selected from a group of lubricants consisting of:
    a mineral-oil based lubricant;
    a petroleum-based lubricant; and
    a shea-based lubricant.

6. The breast pump shield of claim 1, wherein the wiping layer is formed from a cotton-based fabric.

7. The breast pump shield of claim 1, wherein the support layer is formed from a metal foil.

8. The breast pump shield of claim 1, wherein the body portion is formed from a semi-rigid material, wherein the body portion further comprises support surfaces and rods to provide the body portion with rigidity, and wherein the rods are configured to be reusable after disposing of the body portion.

9. The breast pump shield of claim 1, wherein the throat portion comprises a ridged portion that collapses and expands, and wherein the breast pump shield is disposable.

10. The breast pump shield of claim 9, further comprising support surfaces and rods that are used to provide rigidity for the ridged portion and to prevent collapsing of the ridged portion during use of the breast pump shield.

11. The breast pump shield of claim 1, wherein the further lubricant layer is provided to reduce irritation associated with using the breast pump shield by lubricating surfaces that come into contact with the human breast.

12. The breast pump shield of claim 1, wherein the further lubricant layer is configured to allow the nipple to slide along a side wall of the throat portion to stimulate the nipple and to encourage milk flow during pumping.

13. A breast pump shield comprising:
   a body portion comprising a breast engagement portion and a throat portion, wherein the breast engagement portion comprises a ring on an outer surface of the breast engagement portion, wherein the breast engagement portion is configured to receive at least a portion of a human breast of a user, and wherein the throat portion is configured to receive at least a portion of a nipple of the user and to receive milk from the human breast;
   a suction chamber located adjacent to the throat portion, the suction chamber comprising an inlet;
   a first cover located at the ring of the body portion, wherein the first cover comprises a support layer, a lubricant layer adjacent to a first side of the support layer, and a wiping layer located adjacent to a second side of the support layer, wherein the first cover cooperates with the body portion to provide at least part of a hermetic seal for an interior space of the body portion prior to use, and wherein the breast pump shield is disposable, and wherein a further lubricant layer is located within the body portion, the throat portion, and the suction chamber;
   a second cover located over the inlet formed in the suction chamber;
   an assembly structure configured to connect the breast pump shield to a bottle; and
   a third cover located at the assembly structure.

14. The breast pump shield of claim 13, wherein at least one of the lubricant layer or the further lubricant layer comprises a layer of food grade lubricant selected from a group of lubricants consisting of:
   a coconut-based lubricant;
   a flax-seed-based lubricant;
   a fish-oil-based lubricant; and
   a vegetable-based lubricant.

15. The breast pump shield of claim 13, wherein at least one of the lubricant layer or the further lubricant layer comprises a layer of lubricant selected from a group of lubricants consisting of:
   a mineral-oil based lubricant;
   a petroleum-based lubricant; and
   a shea-based lubricant.

16. The breast pump shield of claim 13, wherein the throat portion comprises a ridged portion that collapses and expands.

17. The breast pump shield of claim 13, wherein the further lubricant layer is provided to reduce irritation associated with using the breast pump shield by lubricating surfaces that come into contact with the human breast.

18. A breast pump shield comprising:
   a body portion comprising a breast engagement portion and a throat portion, wherein the breast engagement portion comprises a ring on an outer surface of the breast engagement portion, wherein the breast engagement portion is configured to receive at least a portion of a human breast of a user, and wherein the throat portion is configured to receive at least a portion of a nipple of the user and to receive milk from the human breast;
   a suction chamber located adjacent to the throat portion, the suction chamber comprising an inlet through which a breast pump is connected to the suction chamber; and
   a first cover located at the ring of the body portion, wherein the first cover comprises a support layer, a lubricant layer located adjacent to a first side of the support layer, and a wiping layer located adjacent to a second side of the support layer;
   a further lubricant layer located within the body portion, the throat portion, and the suction chamber;
   a second cover located over the inlet formed in the suction chamber;
   an assembly structure configured to connect the breast pump shield to a bottle; and
   a third cover located at the assembly structure,
   wherein the first cover cooperates with the body portion to provide at least part of a hermetic seal for an interior space of the body portion prior to use and to prevent leakage of the further lubricant layer from the breast pump shield, and wherein the breast pump shield is disposable.

19. The breast pump shield of claim 18, wherein at least one of the lubricant layer or the further lubricant layer comprises a layer of lubricant selected from a group of lubricants consisting of:
   a coconut-based lubricant;
   a flax-seed-based lubricant;
   a fish-oil-based lubricant;
   a vegetable-based lubricant;
   a mineral-oil based lubricant;
   a petroleum-based lubricant; and
   a shea-based lubricant.

20. The breast pump shield of claim 18, wherein the further lubricant layer is provided to reduce irritation associated with using the breast pump shield by lubricating surfaces that come into contact with the human breast.

* * * * *